United States Patent [19]

Porter et al.

[11] Patent Number: 4,594,998
[45] Date of Patent: Jun. 17, 1986

[54] PENILE PROSTHESIS OF IMPROVED MALLEABLE CONSTRUCTION

[75] Inventors: Christopher H. Porter, Minnetonka; Gregory D. Giter, Plymouth; Robert W. Pugh, Jr., Lakeville, all of Minn.

[73] Assignee: American Medical Systems, Inc., Minnetonka, Minn.

[21] Appl. No.: 533,527

[22] Filed: Sep. 16, 1983

[51] Int. Cl.⁴ .............................................. A61F 5/00
[52] U.S. Cl. .......................................... 128/79; 623/66
[58] Field of Search .................. 128/79, 343; 3/1; 604/265–268, 280–284

[56] References Cited

U.S. PATENT DOCUMENTS

| | | | |
|---|---|---|---|
| 2,290,571 | 7/1942 | Peyton | 128/343 |
| 4,066,073 | 1/1978 | Finney et al. | 128/79 |
| 4,151,841 | 5/1979 | Barrington | 128/79 |
| 4,244,370 | 1/1981 | Furlow et al. | 128/79 |
| 4,392,562 | 7/1983 | Burton et al. | 128/79 |
| 4,411,260 | 10/1983 | Koss | 128/79 |
| 4,483,331 | 11/1984 | Trick | 128/79 |

Primary Examiner—Dalton L. Truluck
Assistant Examiner—Mario Costantino
Attorney, Agent, or Firm—Williamson, Bains, Moore & Hansen

[57] ABSTRACT

An implantable penile prosthesis for overcoming male erectile impotence in the form of an elongated cylindrical device of malleable construction. The device is adapted to be implanted within the corpora cavernosa of the penis. A malleable rod capable of holding any shape to which it is bent is encapsulated within a cylindrical insert member made of biocompatible, flexible material. A thin walled sleeve of predetermined wall thickness may be positioned over the outside of the cylindrical insert member in covering relation thereto for adjustment of the outside diameter of the implant device. The cylindrical insert member tapers along its distal end section towards the distal end extremity of the device.

22 Claims, 6 Drawing Figures

PENILE PROSTHESIS OF IMPROVED MALLEABLE CONSTRUCTION

BACKGROUND OF THE INVENTION

This invention relates to implantable prosthetic devices of rod-type construction. In particular, the improved prosthetic device disclosed herein is of the type incorporating a malleable rod which permits the device to be bent between a comfortable, out of the way position and a straight position wherein the penis is held erect for sexual intercourse. Such a penile prosthesis incorporating a malleable rod is disclosed in U.S. Pat. No. 3,987,789 issued on Oct. 26, 1976 to Gerald W. Timm and John H. Burton.

A variation of the surgically implantable malleable penile prosthesis having a limited bend feature is disclosed in U.S. Pat. No. 4,392,562 issued on July 12, 1983. An implantable penile prosthesis incorporating a stiffening bar having a joint bendable from a straight configuration to a curved position in only one direction is disclosed in U.S. Pat. No. 4,177,805 issued on Dec. 11, 1979 to Theodor Tudoriu. A rod type of penile implant comprised of axial sections of varying flexural properties, and including a very flexible hinge section, is disclosed in U.S. Pat. No. 4,066,073 issued to Roy B. Finney et al. U.S. Pat. No. 4,151,840 issued on May 1, 1979 to James E. Barrington discloses still a further version of a mechanical penile prosthesis which is bendable and is comprised of a series of link members coupled to each other in such a way as to permit the prosthesis to be bent between curved and straight configurations.

The evolution of the bendable and malleable types of implantable penile prostheses followed the rigid rod type of penile prosthesis of U.S. Pat. No. 3,893,456 issued to Michael P. Small et al on July 8, 1975. That type of prosthesis incorporates a rigid rod having flexural stiffness which suffers from the disadvantage of holding the penis in substantially a permanent erectile state. The bendable and malleable penile prosthetic devices overcome that particular shortcoming.

A malleable penile prosthesis manufactured in West Germany by Walter Koss OHG and distributed in the United States by Dacomed Corporation of Minneapolis, Minn. is disclosed in a European patent application filed on Nov. 19, 1981 under Application No. 81109752.6 and bearing a disclosure or publication number of No. 0,052,858. That device incorporates a length adjustment feature achieved by using a malleable cylinder which may be cut to various lengths at predetermined increments in combination with a silicone cover which may be pulled over one end of the cylinder.

The malleable penile prosthesis disclosed herein has been developed with a view towards providing a means for readily adjusting the diameter of the implant cylinder to accommodate the physical anatomy of particular patients. Also, the potential problem of damaging the silicone rubber cylinder by the abrading action of a metallic malleable rod encased therein has been overcome by utilizing a special protective sheath around the malleable rod as disclosed herein.

BRIEF SUMMARY OF THE INVENTION

The improved penile prosthesis of this invention is particularly characterized by a malleable construction which ensures long flex life through repeated bending without damage to any component of the structure and which can be readily adapted at the time of use to be the proper size diameter for a patient's penis.

These basic objectives are realized by a penile prosthesis construction comprised of an elongated, cylindrical insert member sized and shaped for easy insertion and a close fit within the corpora cavernosa of the penis, and an elongated malleable rod contained longitudinally within the insert member. The rod has malleable properties which permit it to stay in any shape to which it is bent; yet it is sufficiently rigid to hold a penis erect for sexual intercourse when in a straight configuration.

Advantageously, the cylindrical insert member is made of silicone rubber which is soft enough to be readily bendable and to be able to stay in a downwardly bent, comfortable, out of the way position of the penis without springing back. The malleable rod preferably comprises a twisted bundle of wire strands. Stainless steel wires formed in a cablelike configuration have proven to provide excellent malleability and flex life under repeated bending.

As a particularly beneficial aspect of the invention, the insert member tapers along a distal end section towards its distal tip. This shape not only facilitates insertion of the device, but also permits accommodation of the implant to corpora cavernosa of varying diameters. The insert member is further comprised of a rearwardly tapered proximal end which anchors the device in the body and a substantially straight cylindrical section located between the distal and proximal ends.

Adjustment of the diameter of the device is further provided by a thin walled sleeve positioned over the outside of the insert member in covering relation to at least the portion of its length which lies within the pendulous penis. The sleeve has walls of a predetermined thickness and thus permits the diameter of the implant device to be incrementally adjusted by its selective use or removal. A plurality of such sleeves of incrementally increasing diameter positioned one over the other may be used to enlarge the range of diameter adjustment.

A further advantageous feature resides in the use of a protective sheath between the malleable rod and the soft material of the cylindrical insert member within which the rod is encapsulated. This sheath, preferably made of fabric, protects the silicone rubber insert member against abrasion and wear which could be caused by rubbing contact with the metallic malleable rod.

DESCRIPTION OF THE PREFERRED EMBODIMENTS

Figure 1:
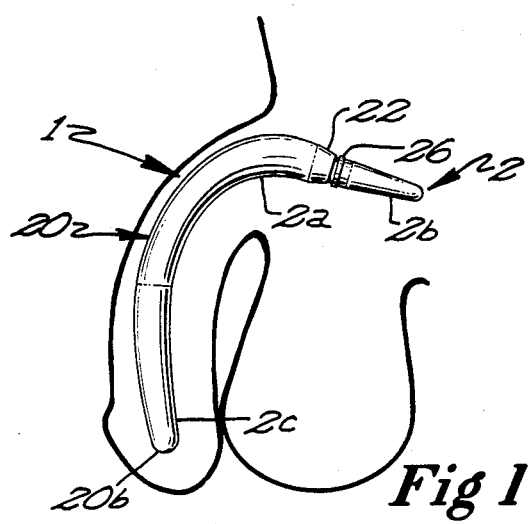
FIG. 1 is a pictorial view of a penis with the prosthetic device implanted therein, with the penis in a comfortable, relatively concealed position.
Figure 2:
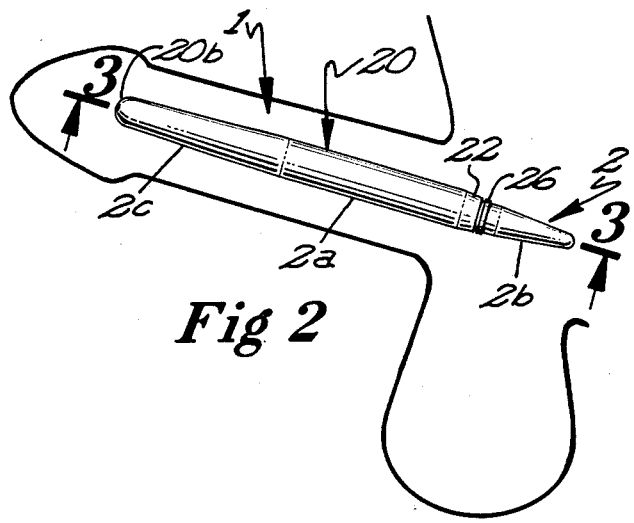
FIG. 2 is a pictorial view similar to FIG. 1, but showing the penis in an erectile state with the implantable device in a straight position.
Figure 3:
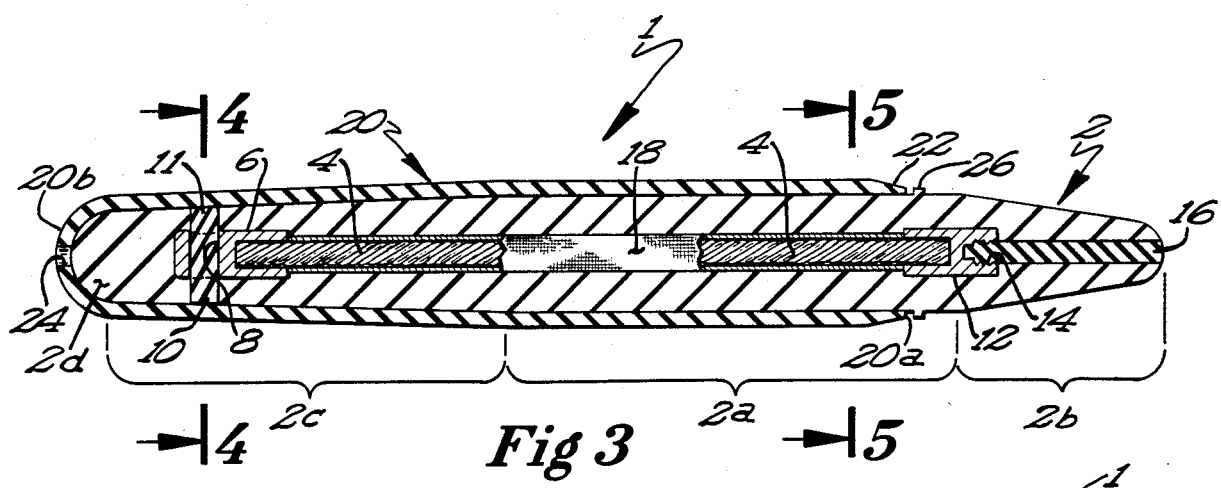
FIG. 3 is a longitudinal, cross section view of the implantable penile prosthesis, taken along lines 3—3 of FIG. 2.
Figure 4:
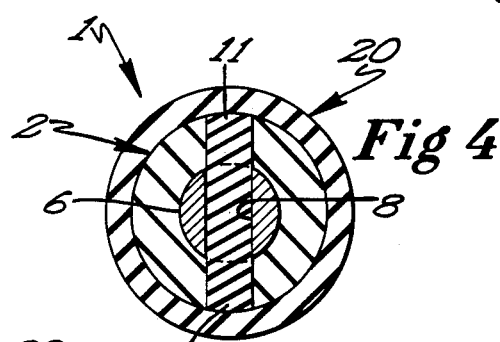
FIG. 4 is a transverse, cross sectional view of the implantable penile prosthesis taken along lines 4—4 of FIG. 3.
Figure 5:
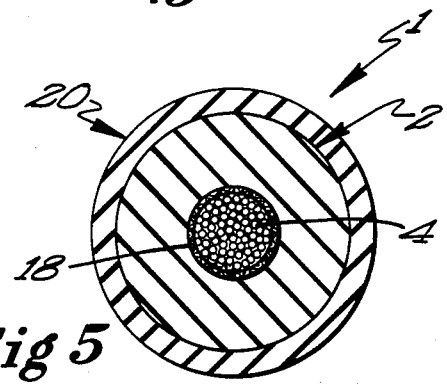
FIG. 5 is a transverse, cross sectional view of the penile prosthesis taken along lines 5—5 of FIG. 3.

With reference to FIGS. 1-3 of the drawings, the implantable penile prosthesis of this invention is generally indicated by reference numeral 1. The prosthesis, as shown, is an elongated cylindrical device adapted for implantation within the penis. It is comprised of an elongated, cylindrical insert member 2 as its main structural component. Cylindrical insert member 2 is made of biocompatible, flexible material, and is sized for insertion within the corpus cavernosum of the penis. Insert member 2 is a solid member, which is, however, sufficiently soft and flexible to avoid trauma upon implantation and use, and to permit its bending as hereinafter set forth. For this purpose, medical grade silicone rubber of the type manufactured under the trade name Silastic by Dow Chemical Company has proven to be particularly usable and effective.

For insertion and anchoring purposes hereinafter set forth, cylindrical insert member 2 is comprised of three basic sections. These include a first substantially straight cylindrical section 2a, which is so designated in FIG. 3, a proximal end section 2b, and a distal end section 2c. Proximal end section 2b tapers rearwardly towards its proximal extremity from its point of juncture with the proximal end of cylindrical section 2a. Distal end section 2c tapers forwardly in a more gradual taper from the distal end of straight cylindrical section 2a, towards distal tip 2d. Section 2a is not tapered, and has a uniform diameter of straight, cylindrical shape as shown in FIG. 2 in the erect condition of the prosthetic device. The rearwardly tapered proximal end 2b serves as an anchoring device. Its taper permits it to be readily implanted in the pubic symphasis of the body of the patient for secure positioning of the prosthetic device. Forwardly tapering, distal end section 2c generally conforms to the similarly tapered front end of the corpora cavernosa of the penis, thereby facilitating the insertion of the device. Also, the forward taper on section 2c permits it to readily adapt to variations in the diameter of the distal corpora cavernosa of a patient. Distal tip 2d of cylindrical insert 2 is rounded and somewhat blunt as shown in FIG. 3 to accommodate its insertion within the glans penis.

Contained within cylindrical member 2 and extending longitudinally therein is a malleable rod 4. Malleable rod 4 is constructed in such a way and of such materials as to permit it to be bent into any desired shape, and to hold the particular configuration into which it is bent. It nevertheless has sufficient rigidity to maintain the penis in an erect condition for sexual intercourse, when the entire prosthetic device is straightened as is illustrated in FIG. 2. These desired properties and capabilities of the malleable rod may be achieved by making it from various materials. Malleable metals such as copper and various alloys could be satisfactory. It has been found that a plurality of stainless steel wire strands twisted into a cablelike configuration as shown in FIG. 3 provide a particularly effective malleable rod which resists fatigue failure and has a long flex life.

Primarily for purposes of molding and assembly, malleable rod 4 is provided with a front or distal end cap 6, and a rear or proximal end cap 12. Front end cap 6 is of generally tubular configuration and is swaged or crimped over the distal end of rod 4 as shown in FIG. 3. End cap 6 has a transverse hole 8 extending therethrough. This hole or bore provides attachment means for a mandrel or other device which is extended transversely therethrough for supporting the front end of rod 4 in a mold cavity. After the mold operation, the transverse bores left in insert member 2 on both sides of cap 6 are plugged with silicone rubber, such silicone rubber plugs being indicated by reference numerals 10 and 11.

The rear end cap 12 for rod 4 is also tubular at its distal end and is crimped or swaged over the rear end of rod 4. A threaded aperture 14 in the proximal end of cap 12 is used to receive a screw or other threaded mandrel type device for supporting the proximal end of rod 4 in a mold cavity. With malleable rod 4 thus supported longitudinally within a mold cavity by a device inserted transversely into bore 8 of front cap 6 and a screwlike device threaded into opposite end cap 12, molding material is injected into the mold around the outside of rod 4. Such material preferably comprises medical grade silicone rubber, as noted above. Such a molding operation forms cylindrical insert 2 with malleable rod 4 completely encapsulated therein.

After the molding operation, the devices utilized to support rod 4 within the mold cavity are removed from end caps 6 and 12. The axial hole left in the distal end section 2b of insert member 2, when the screw or threaded mandrel is removed from threaded aperture 14 of end cap 12, is filled by silicone to provide an elongated, axial plug 16. As noted above, the bore segments on either side of front end cap 6 are filled by silicone plugs 10 and 11.

As may best be seen by reference to FIG. 3, a protective sheath 18 is utilized to cover malleable rod 4. Sheath 18 assumes a generally tubular configuration as shown, and is disposed between malleable rod 4 and the adjacent, inner surface of cylindrical insert member 2. In this way sheath 18 serves to protect the rubber material of insert member 2 from being worn and abraded by migration of malleable rod 4. To that end protective sheath 18 has been made out of fabric. In particular, Teflon coated and/or impregnated polyester has been found to be effective. Such material is substantially the same as or very similar to surgical suture.

In order to provide a means for selectively adjusting the diameter of the implantable penile prosthesis to most closely approximate the diameter required for particular patients, a plastic sleeve 20 is removably positioned over the outside of cylindrical insert member 2. Although various materials may be utilized for sleeve 20, silicone rubber of the same basic composition as that utilized for insert member 2 has proven to be particularly desirable. Sleeve 20 is of thin-walled construction. The walls are of a predetermined thickness to provide an adjustment in diameter as desired. For example, if sleeve 20 has a wall thickness of one millimeter, it will add two millimeters to the diameter of the penile prosthesis. Thus, if the outside diameter of cylindrical segment 2a of insert member 2 is nine millimeters, an increase in diameter to eleven millimeters can be achieved by utilizing sleeve 20 over the outside of cylindrical insert 2. It also is to be noted that an additional increment of diametrical adjustment can be achieved for the patient because of the taper in the distal end section 2c of insert member 2. This taper is such, for example, that the diameter of cylindrical member 2 decreases by approximately two millimeters from the distal end of cylindrical segment 2a to the distal tip of the device.

It is also contemplated that more than one sleeve may be placed over the outside of cylindrical insert member 2 in order to achieve a greater range of adjustment in the diameter of the prosthetic insert device. The sleeves would be identical to sleeve 20, except that the sleeves would incrementally increase in diameter. They would be removably positioned, one over the outside of the other, and would extend over the same length of insert member 2 as does sleeve 20. By providing each successively greater diameter sleeve with a predetermined wall thickness, a desired outer diameter greater than that of cylindrical insert 2 can be achieved by using the appropriate number of sleeves.

Sleeve 20 has a fully open, proximal end 20a, and a rounded distal tip 20b. Distal tip 20b covers, and substantially conforms to the shape of distal tip 2d of insert member 2 as shown in FIG. 3. The open, proximal end 20a of sleeve 20 terminates distally forwardly of tapered proximal end 2b of insert member 2, closely adjacent thereto. Since proximal end 2b of the insert 2 will be anchored within the body of the patient as illustrated in FIGS. 1 and 2, sleeve 20 will extend over the entire length of the pendulous portion of the penis when the device is implanted as shown in FIGS. 1 and 2. This is accomplished by having sleeve 20 of such a length that it will come substantially up to the distal end of tapered proximal tip 2b.

Sleeve 20 is placed on cylindrical insert member 2 by pulling it over the distal end of the insert member. A through hole 24 is provided in the distal tip 2d of sleeve 20 to permit air to escape during this assembly procedure. This makes it somewhat easier to pull sleeve 20 over the outside of insert member 2. To further facilitate the assembly procedure of sleeve 20 to cylindrical insert 2, sleeve 20 is first soaked in a liquid such as freon to expand it. Thus expanded, sleeve 20 is slipped over the distal end of insert member 2 and pulled rearwardly until it abuts against a stop and locating annular shoulder 26. Shoulder 26 is located at the proximal end of straight cylindrical segment 2a of insert member 2, just forwardly of tapered proximal end 2b. Sleeve 20 shrinks after being pulled onto the insert member 2, to ultimately provide a tight fit over the outer surface thereof. The shrinking of sleeve 20 may cause a small circumferential gap as shown in FIG. 3 between stop shoulder 26 and the proximal end 20a of sleeve 20. It is to be noted that the proximal end of sleeve 20 is tapered slightly at 22 in order to provide a smooth transition into tapered proximal end 2b of insert member 2. Stop and locating shoulder 26 is particularly useful and beneficial in controlling the extent to which sleeve 20 is pulled on to cylindrical insert member 2. If sleeve 20 is pulled on too far it will be stretched, and its wall thickness will thus be reduced. As a result, the desired diametrical adjustment will not be accomplished.

Figure 6:
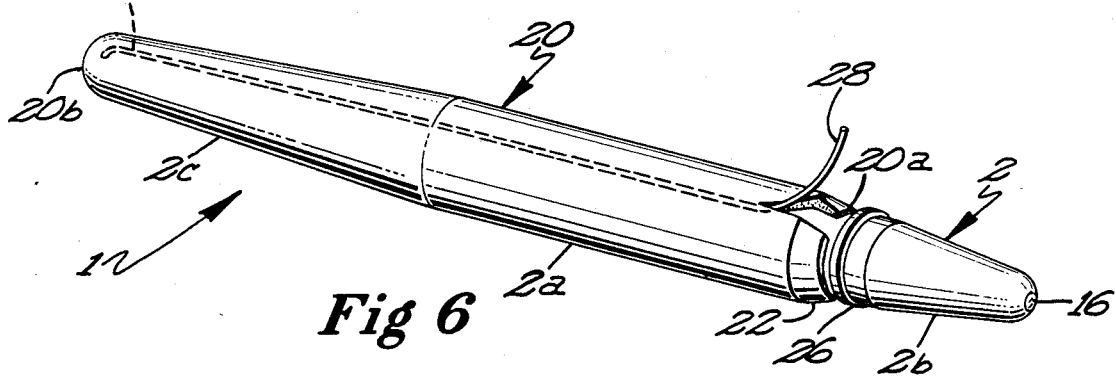
FIG. 6 is a fragmentary, perspective view of the implantable penile prosthesis showing a tear thread for removing the outer sleeve.

It is anticipated that the penile prosthesis will normally be sold with sleeve 20 in place on cylindrical insert member 2. If the added diameter provided by sleeve 20 is not desired, the surgeon may remove it. Sleeve 20 is made of silicone rubber material which is sufficiently soft, flexible, and pliant to facilitate its being removed from insert member 2. Removal can be assisted by the slitting of sleeve 2 with a knife. To further facilitate the removal of sleeve 20, a suture tear strip or thread 28 may be molded in to the wall of sleeve 20 as illustrated in FIG. 6. To ensure tearing through the entire wall thickness of sleeve 20, pull thread or suture strip 28 will be located along the inside, bottom extremity of sleeve 20 as shown. A short length of pull thread 28 will be exposed beyond the proximal end 20a of sleeve 20 for gripping, and thread 28 will then be pulled forwardly towards the distal end of the implant device to completely sever sleeve 20 and to permit its easy removal.

The malleable penile prosthesis disclosed herein may be implanted in pairs within the corpora cavernosa following known surgical techniques for the implantation of rod-type penile prosthetic devices. Reference is made to U.S Pat. Nos. 3,987,789 and 3,893,456 for a disclosure of implantation techniques which may be utilized. The incision for obtaining access to the corpora cavernosa may be made at different locations, as prove to be most suitable for the particular patient. The various surgical options include a circumcisional incision by the corona near the glans penis, a scrotal incision, an infrapubic approach wherein an incision is made just below the pubic bone, a mid-shaft incision, or a perineal incision.

A surgical suture or thread may be utilized to assist in pulling the prosthetic cylinders into the corpora cavernosa. The crossbore extending transversely through the distal end of cylindrical member 2 is particularly useful for that purpose. That crossbore is defined by the cavity or hole 8 within end cap 6, as well as by aligned plugs 10 and 11 of silicone rubber which are utilized to fill the crossbore after the molding operation. In actual practice, hole or cavity 8 in end cap 6 will also be partially if not completely filled with silicone rubber during the plugging operation. A surgical needle having a thread or suture attached to it can be readily passed through the crossbore defined by silicone plugs 10 and 11 and transverse hole or bore 8. If size adjustment sleeve 20 is still in place on the prosthetic device at the time of implantation, the surgical needle may readily be pierced through its opposite side walls to complete a threaded loop completely through the prosthetic implant device. It is anticipated that such a pull thread or suture may be effectively utilized in conjunction with an insert tool as disclosed in U.S. Pat. No. 4,244,370 issued to William L. Furlow and Michael A. Mikulich for positioning the malleable penile prosthesis cylinders within the corpora cavernosa.

After implantation, the penis will normally be positioned in a comfortable, out of the way position as shown in FIG. 1. In such a position the malleable insert cylinders will be bent downwardly as shown. The tapered proximal end 2b of the implant cylinders will be located as shown within the body of the patient in the pubic symphasis to assist in anchoring the implant cylinders in place. As the penis is manually manipulated to an upright, straight position as shown in FIG. 2, proximal end 2b will remain as a firm anchor in the same position as shown in FIG. 1. The malleable implant cylinders will bend along the length of the distal portion thereof, primarily within the length of the tapered distal end section 2c.

It is anticipated that various modifications and changes may be made in the size, shape, and structure of the malleable penile prosthesis as disclosed herein without departing from the spirit and scope of the invention as defined by the following claims.

What is claimed is:

1. An implantable penile prosthesis comprising:
   an elongated, generally cylindrical insert member made of biocompatible, flexible material, said member being of integral construction and sized to extend over substantially the entire length of the corpus cavernosum of the penis within which it is inserted and said member having a distal tip of reduced diameter shaped to adapt to the glans penis and a proximal end constructed to anchor within the pubic symphasis;

an elongated, malleable rod fully enclosed and contained over its entire length within said cylindrical insert member and extending longitudinally therein, said malleable rod being bendable to various shapes and positions and having the physical capability of holding any shape to which it is bent and having sufficient rigidity to hold a penis erect for sexual intercourse when in a straight position; and a thin walled sleeve of biocompatible material removably positioned over the outside of said cylindrical insert member in closely conforming, covering relation to at least the length of said insert member which will lie within the pendulous portion of the penis, and the walls of said sleeve having a predetermined thickness to provide a penile prosthesis of desired diameter as required for particular patients.

2. An implantable penile prosthesis as defined in claim 1 wherein:
said cylindrical insert member distal tip has a rounded, blunt, distal end extemity for accommodation within the glans penis, and said sleeve has a rounded distal tip positioned in covering relation to said distal end of said insert member, said sleeve providing an uninterrupted, uniformly smooth outer surface on said prosthesis over at least the length thereof within the pendulous portion of the penis.

3. An implantable penile prosthesis as defined in claim 2 wherein:
said distal tip of said sleeve has a hole therethrough.

4. An implantable penile prosthesis as defined in claim 1 wherein:
said sleeve is made of material which is sufficiently soft, flexible, and pliant to permit said sleeve to be stripped from said insert member if it is not desired.

5. An implantable penile prosthesis as defined in claim 4 wherein:
said sleeve is made of medical grade, silicone rubber.

6. An implantable penile prosthesis as defined in claim 1 wherein:
said sleeve is shrunk fit over said insert member in tight covering relation thereto.

7. An implantable penile prosthesis as defined in claim 1 wherein:
said sleeve has an open proximal end; and
said insert member has an annular stop shoulder on its proximal end for locating the desired position of said open, proximal end of said sleeve thereon.

8. An implantable penile prosthesis as defined in claim 1 wherein:
a protective sheath of fabric material of minimal bending modulus covers said malleable rod, said sheath being disposed between said malleable rod and said cylindrical insert member, and imparting no additional rigidity to the malleable penile prosthesis.

9. An implantable penile prosthesis as defined in claim 8 wherein:
said protective sheath is made of teflon coated polyester fabric.

10. An implanatable penile prosthesis as defined in claim 8 wherein:
said malleable rod is comprised of a twisted bundle of wire strands formed in a cable configuration.

11. An implantable penile prosthesis as defined in claim 1 wherein:
said insert member is made of silicone rubber.

12. An implantable penile prosthesis as defined in claim 10 wherein:
said wire strands are stainless steel.

13. An implantable penile prosthesis as defined in claim 1 wherein:
said sleeve has an open proximal end; and
said proximal end of said insert member tapers rearwardly towards its proximal extremity to assist in anchoring said prosthesis within the pubic symphasis of the body of the patient, and said open proximal end of said sleeve terminates distally forwardly of said tapered proximal end of said insert member closely adjacent thereto.

14. An implantable penile prosthesis as defined in claim 1 wherein:
said insert member has a rounded distal end extremity, and said insert member tapers towards said distal end extremity from a point along the length of said insert member between said proximal end and said distal end extremity.

15. An implantable penile prosthesis as defined in claim 14 wherein:
said insert member is comprised of a cylindrical segment of uniform diameter located between said proximal end and said distal end extremity, and a distal end section extending between said cylindrical segment and said distal end extremity, and said taper is along the length of said distal end section.

16. An implantable penile prosthesis as defined in claim 1 wherein:
a pull thread having a freely exposed end is contained within the wall of said sleeve, said thread extending along substantially the entire length of said sleeve, whereby said sleeve may be severed for removal by pulling said thread.

17. An implantable penile prosthesis as defined in claim 1 wherein:
a plurality of sleeves of biocompatible material are removably positioned over the outside of said cylindrical insert member, one over the other, in covering relation to at least the length of said insert member which will lie within the pendulous portion of the penis, said sleeves incrementally increasing in diameter to provide a range of adjustment as to the overall diameter of said penile prosthesis.

18. An implantable penile prosthesis as defined in claim 1 wherein:
said sleeve has an open proximal end which terminates adjacent the proximal end of said insert member.

19. An implantable penile prosthesis as defined in claim 1 wherein:
said cylindrical insert member is made of solid but flexible and pliant material, and has a crossbore extending transversely therethrough adjacent to its distal end, said distal end being rounded at its tip and being adapted to be inserted within the glans penis whereby a suture thread may be passed through said crossbore and utilized to pull said penile prosthesis into proper position within the corpora cavernosa of the penis, said sleeve being positioned over the outside of said cylindrical insert member in covering relation to said crossbore.

20. An implantable prosthesis as defined in claim 2 wherein:
said sleeve is of uniform wall thickness over its entire length including its rounded distal tip and closely conforms to the shape of said distal end extremity of said cylindrical insert member and to said pendulous portion length of said insert member in a snug fit therewith.

21. An implantable penile prosthesis comprising:
an elongated, generally cylindrical insert member made of biocompatible, flexible material, said member being of integral construction and sized to extend over substantially the entire length of the corpus cavernosum of the penis within which it is inserted, and said member having a distal tip of reduced diameter shaped to adapt to the glans penis and a proximal end constructed to anchor within the pubic symphasis; and
a thin walled sleeve of biocompatible material removably positioned over the outside of said cylindrical insert member in closely conforming, covering relation to at least the length of said insert member which will lie within the pendulous portion of the penis, and the walls of said sleeve having a predetermined thickness to provide a penile prosthesis of desired diameter as required for particular patients.

22. An implantable penile prosthesis as defined in claim 21 wherein:
said cylindrical insert member has a rounded, blunt, distal end for accommodation within the glans penis, and said sleeve has a rounded distal tip positioned in covering relation to said distal end of said insert member, said sleeve providing an uninterrupted, uniformly smooth outer surface on said prosthesis over at least the length thereof within the pendulous portion of the penis.

* * * * *